United States Patent [19]

Staendeke et al.

[11] 4,098,872
[45] Jul. 4, 1978

[54] STABILIZED RED PHOSPHORUS AND PROCESS FOR MAKING IT

[75] Inventors: Horst Staendeke; Franz-Josef Dany; Joachim Kandler; Werner Klose, all of Erftstadt, Fed. Rep. of Germany

[73] Assignee: Hoechst Aktiengesellschaft, Frankfurt am Main, Fed. Rep. of Germany

[21] Appl. No.: 797,190

[22] Filed: May 16, 1977

[30] Foreign Application Priority Data

May 19, 1976 [DE] Fed. Rep. of Germany ....... 2622296

[51] Int. Cl.² ............................................. C01B 25/00
[52] U.S. Cl. ..................................... 423/265; 149/29; 252/400 A; 423/322
[58] Field of Search ..................... 423/265, 322; 149/6, 149/29; 252/400 A

[56] References Cited

U.S. PATENT DOCUMENTS

| | | | |
|---|---|---|---|
| 2,399,120 | 4/1946 | Hurd | 423/322 |
| 2,440,303 | 4/1948 | Silverstein | 423/322 |
| 2,574,466 | 11/1951 | Clay et al. | 149/29 |
| 3,488,711 | 1/1970 | Dany et al. | 149/29 |
| 3,657,027 | 4/1972 | Horsey et al. | 149/29 |
| 3,884,734 | 5/1975 | Palmer et al. | 149/6 |
| 3,974,260 | 8/1976 | Wortmann et al. | 423/265 |

FOREIGN PATENT DOCUMENTS 1,141,213  1/1969  United Kingdom ................ 423/322

*Primary Examiner*—Earl C. Thomas
*Assistant Examiner*—Eugene T. Wheelock
*Attorney, Agent, or Firm*—Connolly and Hutz

[57] ABSTRACT

The invention provides stabilized pulverulent red phosphorus. It comprises a homogeneous blend of red phosphorus particles with a size of at most about 2 mm and a metal compound of the second or third group of the Periodic System as an oxidation stabilizer, wherein the metal compound is the aluminum, magnesium, calcium or zinc salt of an acid orthophosphoric acid ester of a long chain aliphatic alcohol, which may be ethoxylated, or phenol, the metal compound being present in the homogeneous blend in a proportion of about 0.25 to 5 weight %.

17 Claims, No Drawings

STABILIZED RED PHOSPHORUS AND PROCESS FOR MAKING IT

The present invention relates to stabilized red phosphorus and to a process for making it, wherein red phosphorus, which is preferably in the form of an aqueous suspension, is treated with a metal salt of an acid orthophosphoric acid ester as a stabilizing agent.

It has been described that red phosphorus undergoes in moist atmosphere a chemical surface reaction involving oxidation and disproportionation with the resultant formation of various acids of phosphorus (oxidation stages +1 and +5) and hydrogen phosphide.

As described by Gmelin, Handbuch der anorganischen Chemie, 8th edition (1964), vol. phosphorus, part B, page 83, Verlag Chemie, Weinheim (Bergstrasse), red phosphorus can be stabilized by means of aluminum hydroxide which is precipitated on the phosphorus particles by the consecutive addition of aqueous 10% sodium hydrogen phosphate and aluminum sulfate solutions heated to 55° – 60° C. The resulting aqueous suspension is filtered and dried. This process is, however, not satisfactory in respect of the following points. The disproportionately large quantities of aluminum hydroxide which are necessary to produce a satisfactory stabilizing effect contaminate the phosphorus to an unacceptable extent and adversely affect is further widespread uses.

A further process for stabilizing red phosphorus has been described in U.S. Pat. No. 2,359,243, wherein red phosphorus is suspended in a 0.4 normal solution of sodium aluminate. Next, a stream of air is passed for 10 hours at 85° to 90° C through the suspension, which is filtered, washed with hot water and dried under vacuum.

A still further process for stabilizing red phosphorus has been disclosed in U.S. Pat. No. 2,635,953, wherein aluminum hydroxide is used in combination with zinc or magnesium hydroxide.

The processes last described do equally not permit red phosphorus to be satisfactorily stabilized against oxidation with the use of a minimum of stabilizer.

In accordance with our present invention, we have unexpectedly found that red phosphorus can be satisfactorily stabilized by precipitating a minor proportion of a metal salt of an acid orthophosphoric acid ester on the surface of red phosphorus.

The present invention relates more particularly to stabilized pulverulent red phosphorus consisting of a homogeneous blend of red phosphorus particles with a size of at most about 2 mm and a metal compound of the second or third group of the Periodic System as an oxidation stabilizer, wherein the metal compound is the aluminum, magnesium, calcium or zinc salt of an acid orthophosphoric acid ester of a long chain aliphatic alcohol, which may be ethoxylated, or phenol, the metal compound being present in the homogeneous blend in a proportion of about 0.25 to 5 weight %.

The red phosphorus is preferably used in the form of particles with a size of about 0.01 to 0.15 mm and in admixture with the neutral aluminum, magnesium, calcium or zinc salt of an acid orthophosphoric acid mono- and/or diester of lauryl alcohol tetraethylene glycolether, stearyl alcohol or phenol hexaethylene glycol, the homogeneous blend containing the ester salt in proportions of 0.25 to 3 weight %.

The invention also relates to a process for making stabilized pulverulent red phosphorus consisting of a homogeneous blend of red phosphorus particles with a size of at most 2 mm and a metal compound of the second or third group of the Periodic System as an oxidation stabilizer, which comprises: intimately blending red phosphorus particles with a particle size of at most about 2 mm with about 0.25 to 5 weight % of an acid orthophosphoric acid ester of a long chain aliphatic alcohol, which may be ethoxylated, or phenol; suspending the blend in water and heating the resulting suspension to about 60° to 95° C; gradually admixing the suspension with at least stoichiometric proportions of an aqueous solution of a water-soluble aluminum, magnesium, calcium or zinc salt to cause precipitation of the respective salt of the orthophosphoric acid ester; filtering the resulting mixture, and drying the filter residue at elevated temperature and, if desired, under reduced pressure.

The red phosphorus is more preferably used in the form of particles having a size of about 0.01 to 0.15 mm and its aqueous suspension is preferably heated to a temperature of 80° to 90° C. A further preferred feature of the present process provides for the acid orthophosphoric acid ester of the long chain aliphatic alcohol, which may be ethoxylated, or phenol to be used in a proportion of 1 to 3 weight %, based on red phosphorus, and to be selected from the orthophosphoric acid mono- and/or diester of lauryl alcohol tetraethyleneglycol ether, stearyl alcohol or phenol hexaethyleneglycol ether.

The ester salt of orthophosphoric acid may be prepared, for example, with the use of $Al_2(SO_4)_3 \cdot 18\ H_2O$, $Ca(NO_3)_2 \cdot 4\ H_2O$, $ZnSO_4 \cdot 7\ H_2O$ or $MgSO_4 \cdot 7\ H_2O$, the salt being used in the form of aqueous 5 to 20 weight % solutions.

To prepare the calcium, zinc or magnesium salt of the acid orthophosphoric acid ester, it is good practice to precipitate the ester salt from the aqueous suspension within a certain pH-range as these ester salts are partially soluble in an acid aqueous medium. The zinc salt should more preferably be precipitated from the aqueous suspension at a pH-value of 5.0 to 5.5, and the calcium or magnesium salt should be precipitated at a pH-value of 7.0 to 7.5.

A further preferred feature of the present process finally provides for the filter residue obtained after filtration of the aqueous suspension to be dried at a temperature of 80° to 130° C.

The following statements are intended further to illustrate the process of the present invention.

The mixtures of mono- and diesters of orthophosphoric acid, which are useful as starting materials in the present invention, can be made by the process disclosed in German Patent Specification No. 1 226 101. This process for making mixtures of mono- and diesters of othophosphoric acid from phosphorus pentoxide and alcohols or phenols comprises reacting phosphorus pentoxide with a mixture of the orthophosphoric acid mono- and diesters of the respective alcohol or phenol, which may carry a reaction-inert substituent, in a molar ratio of less than 1:2, preferably 1:3 to 1:6, and further reacting the resulting acid polyphosphoric acid esters with a quantity of alcohol or phenol corresponding to the phosphorus pentoxide used and to the composition desired for the ester mixture, the two reaction steps being effected at temperatures of 20° to 100° C, preferably 40° to 60° C.

The stabilized red phosphorus and the process of the present invention for making such phosphorus compare favorably with the prior art methods inasmuch as considerably less stabilizer is required to be used than heretofore for producing a satisfactory stabilizing effect.

The following Examples illustrate the invention.

EXAMPLE 1

(a) Preparation of a mixture of orthophosphoric acid mono- and diesters of lauryl alcohol tetraethyleneglycol ether. 1000 g of lauryl alcohol tetraethyleneglycol ether, which was obtained by the additive combination of about 4 mols of ethylene oxide with lauryl alcohol and which had a hydroxyl number of 43.6 mg KOH/g, was placed in a heatable stirring vessel, and heated to 30° C under nitrogen. 121.2 g of phosphorus(V)oxide was introduced with the exclusion of moisture, and the reaction mixture was maintained at a temperature of at most 60° C, by cooling if necessary or convenient. Following the addition of $P_4O_{10}$, the mixture was stirred for 2 hours at 65° C and for a further 2 hours at 85° to 90° C, cooled and placed in a container. The liquid slightly yellowish product had a density of 1.02 g/cm$^3$, an acid number of 128 mg KOH/g, and contained 10.9 weight % of $P_2O_5$.

(b) Stabilization of red phosphorus with the use of the aluminum salt of the product made as described under 1 (a) above.

100 g of fine pulverulent red phosphorus (mean particle size = 0.05 mm) was suspended in 500 cc of water and the suspension was heated to 90° C. Next, 2.5 g of a mixture of the orthophosphoric acid monoester and diester of lauryl alcohol tetraethyleneglycol ether (mixing ratio = about 1:1) was stirred into the aqueous suspension which was then admixed dropwise, while stirring was continued, with 50 cc of an aqueous aluminum sulfate solution containing 5 g of $Al_2(SO_4)_3 \cdot 18$ $H_2O$. After a post-reaction period of 1 hour, the aqueous suspension was filtered, the filter residue was washed with water and dried at 80° C in a stream of nitrogen.

The red phosphorus so treated was tested for its stability to oxidation. To this end, a three necked round flask provided with a tubular gas inlet, thermometer, reflux condenser and magnetic stirrer was charged with 450 cc of water and 1 g of red phosphorus, the mixture was heated to 85° C and 10 l of oxygen was introduced thereinto with agitation. A gas mixture consisting of oxygen and hydrogen phosphide (the latter, which was obtained together with acids of phosphorus of various oxidation stages, was formed by disproportionation of red phosphorus) left the reflux condenser. It was delivered to two seriesconnected wash bottles, which each contained 100 cc of a 5 weight % aqueous mercury(II)-chloride solution. The hydrogen phosphide underwent reaction with the mercury(II)chloride in accordance with the following equation:

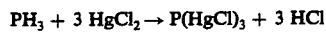

The quantity of oxo acids of phosphorus present in the aqueous suspension of red phosphorus and the quantity of hydrochloric acid present in the gas washing bottles were determined as an index of the stability to oxidation of red phosphorus. The content of phosphoric acid and the content of hydrochloric acid were determined by titration. The results obtained are indicated in the Table hereinafter.

EXAMPLE 2

The procedure was as in Example 1 (b) but the aqueous suspension was admixed dropwise with 50 cc of an aqueous calcium nitrate solution which contained 10 g of $Ca(NO_3)_2 \cdot 4$ $H_2O$ and which replaced the aluminum sulfate solution. In order to completely precipitate the orthophosphoric acid ester salt, the aqueous suspension was admixed with a 5 weight % aqueous sodium hydroxide solution to establish a pH-value of 7. The data determined for the stability to oxidation of the red phosphorus are indicated in the Table hereinafter.

EXAMPLE 3

The procedure was as in Example 1 (b) but the aqueous suspension was admixed dropwise with 50 cc of an aqueous zinc sulfate solution which contained 5 g of $ZnSO_4 \cdot 7$ $H_2O$ and which replaced the aluminum sulfate solution. In order to completely precipitate the orthophosphoric acid ester salt, the aqueous suspension was admixed with a 5 weight % aqueous sodium hydroxide solution to establish a pH-value of 5.5. The data determined for the stability to oxidation of the red phosphorus are indicated in the Table hereinafter.

EXAMPLE 4

(a) Preparation of the orthophosphoric acid monoester of lauryl alcohol tetraethyleneglycol ether. 1172 g of lauryl alcohol tetraethyleneglycol ether, which was obtained by the additive combination of about 4 mols of ethylene oxide with lauryl alcohol and which had a hydroxyl number of 43.6 mg KOH/g, was placed in a heatable stirring vessel, and heated to 30° C under nitrogen. The heated matter was admixed dropwise within 30 minutes with 338 g of polyphosphoric acid which contained 84.1 weight % of $P_2O_5$, was heated to 40° C and came from a heated dosing funnel, and the reaction mixture was maintained at a temperature of at most 60° C. Next, the mixture was stirred for 2 hours at 65° C and for a further 2 hours at 80° to 85° C, cooled and placed in a container.

The slightly brownish product had a density of 1.14 g/cm$^3$ at 20° C, an acid number of 328 mg KOH/g, and contained 20.8 weight % of $P_2O_5$.

(b) Stabilization of red phosphorus with the use of the aluminum salt of the product made as described under 4 (a) above.

100 g of fine pulverulent red phosphorus (mean particle size = 0.05 mm) was suspended in 500 cc water and the suspension was heated to 90° C. Next, 2.5 g of the orthophosphoric acid monoester of lauryl alcohol tetraethyleneglycol ether was stirred into the aqueous suspension which was then admixed dropwise, while stirring was continued, with 50 cc of an aqueous aluminum sulfate solution containing 5 g of $Al_2(SO_4)_3 \cdot 18$ $H_2O$. After a post-reaction period of 1 hour, the aqueous suspension was filtered, the filter residue was washed with water and dried at 80° C in a stream of nitrogen.

The data determined for the stability to oxidation of the red phosphorus so treated are indicated in the Table hereinafter.

EXAMPLE 5

(a) Preparation of the sodium salt of the orthophosphoric acid monoester of stearyl alcohol.

1080 g of stearyl alcohol, 212 g of sodium carbonate and 284 g of phosphorus(V)oxide were mixed at room temperature and with the exclusion of moisture in a kneader and heated. At about 60° C, the mixture commenced softening and foaming which was accompanied by the evolution of carbon dioxide. The reaction was continued by heating to 80° C until $CO_2$ ceased to be evolved, and a pasty product was obtained which solidified upon cooling to about 70° C and which was comminuted by means of the kneader to a fine powder.

The ester salt contained 18.8 weight % of $P_2O_5$ (calculated: 19.1 weight %), 0.1 weight % of $CO_2$ and 0.7 weight % of $H_2O$. The content of orthophosphate and the content of pyrophosphate were determined by paper chromatography and found to be 6.9 weight %, calculated as $NaH_2PO_4$, and 5.6 weight %, calculated as $Na_2H_2P_2O_7$.

(b) Stabilization of red phosphorus with the use of the aluminum salt of the product made as described under 5 a) above.

100 g of fine pulverulent red phosphorus (mean particle size = 0.05 mm) was suspended in 500 cc of water and the suspension was heated to 90° C. Next, 2.5 g of the orthophosphoric acid monoester of stearyl alcohol, which was used in the form of its sodium salt, was stirred into the aqueous suspension which was then admixed dropwise, while stirring was continued, with 50 cc of an aqueous aluminum sulfate solution containing 5 g of $Al_2(SO_4)_3 \cdot 18\ H_2O$. After a post-reaction period of 1 hour, the aqueous suspension was filtered, the filter residue was washed with water and dried at 80° C in a stream of nitrogen.

The data determined for the stabilization of the red phosphorus so treated are indicated in the Table hereinafter.

EXAMPLE 6

(a) Preparation of a mixture of orthophosphoric acid mono- and diesters of phenol hexaethyleneglycol ether.

1000 g of phenol hexaethyleneglycol ether, which was obtained by the additive combination of about 6 mols of ethylene oxide with phenol and which had a hydroxyl number of 43.4 mg KOH/g, was reacted with 121.g of phosphorus(V)oxide, as described in Example 1 (a).

The liquid slightly yellowish product had a density of 1.20 g/cm$^3$ at 20° C, an acid number of 126 mg KOH/g, and contained 10.6 weight % of $P_2O_5$.

(b) Stabilization of red phosphorus with the use of the calcium salt of the product made as described under 6 a) above.

100 g of fine pulverulent red phosphorus (mean particle size = 0.05 mm) was suspended in 500 cc of water and the suspension was heated to 90° C. Next, 5 g of a mixture of the orthophosphoric acid monoester and diester of phenol hexaethyleneglycol ether (mixing ratio = about 1:1) was stirred into the aqueous suspension which was then admixed dropwise, while stirring was continued, with 50 cc of an aqueous calcium nitrate solution containing 10 g of $Ca(NO_3)_2 \cdot 4\ H_2O$.

In order to completely precipitate the orthophosphoric acid ester salt, the aqueous suspension was admixed with a 5 weight % aqueous sodium hydroxide solution so as to establish a pH-value of 7. The data determined for the stability to oxidation of the red phosphorus so treated are indicated in the Table hereinafter.

EXAMPLE 7

The procedure was as in Example 6 (b) but the aqueous suspension was admixed dropwise with 50 cc of an aqueous zinc sulfate solution which contained 10 g of $ZnSO_4 \cdot 7\ H_2O$ and which replaced the calcium nitrate solution. In order to completely precipitate the orthophosphoric acid ester salt, the aqueous suspension was admixed with a 5 weight % aqueous sodium hydroxide solution so as to establish a pH-value of 5.5. The data determined for the stability to oxidation of the red phosphorus so treated are indicated in the Table hereinafter.

EXAMPLE 8 (Comparative Example)

100 g of fine pulverulent red phosphorus was suspended in 500 cc of water. The suspension was heated to 90° C and admixed, with agitation, with 65.5 g of aluminum sulfate $(Al_2(SO_4)_3 \cdot 18\ H_2O)$. Next, a pH-value of 7 was established by the addition of a 5 weight % aqueous sodium hydroxide solution. After a post-reaction period of 1 hour at 90° C, the red phosphorus was filtered, washed with water and dried at 80° C in a stream of nitrogen.

The stability to oxidation of the red phosphorus so treated was determined in the manner described in Example 1 (b). The results obtained are indicated in the Table hereinafter.

EXAMPLE 9 (Comparative Example)

The procedure was as in Example 8, but 196.5 g of $Al_2(SO_4)_3 \cdot 18\ H_2O$ was used.

The data determined for the stability to oxidation of the red phosphorus so treated are indicated in the following Table.

TABLE

| Example | A | B |
|---------|------|-----|
| 1 | 0.07 | 1.2 |
| 2 | 0.19 | 3.7 |
| 3 | 0.24 | 3.8 |
| 4 | 0.07 | 1.2 |
| 5 | 0.32 | 4.0 |
| 6 | 0.34 | 4.8 |
| 7 | 0.25 | 4.0 |
| 8 | 0.19 | 2.8 |
| 9 | 0.09 | 1.1 |

The figures in column A of the above Table indicate the quantity of hydrogen phosphide (mg $PH_3 g \cdot h$) which is evolved on subjecting the phosphorus specimens to oxidation.

The figures in columm B of the above Table relate to the acidity of the aqueous phosphorus-containing suspensions, which is caused by the formation of phosphoric acids on subjecting the red phosphorus to oxidation (mg KOH/g $\cdot$ h).

The Table clearly shows that the low oxidation values obtainable in accordance with this invention on subjecting red phosphorus to oxidation are reproducible with known oxidation stabilizers only if the red phosphorus is admixed with a quantity of conventional stabilizer which is a multiple of the quantity of the oxidation stabilizer used in accordance with this invention:

We claim:

1. Stabilized pulverulent red phosphorus comprising a homogeneous blend of red phosphorus particles with a size of at most about 2 mm and as an oxidation stabilizer the aluminum, magnesium, calcium or zinc salt of an acid orthophosphoric acid ester of a long chain aliphatic alcohol or phenol, the salt being present in the homogeneous blend in a proportion of about 0.25 to 5 weight %.

2. Red phosphorus as claimed in claim 1, wherein the particles have a size of about 0.01 to 0.15 mm.

3. Red phosphorus as claimed in claim 1, wherein the acid orthophosphoric acid ester is the orthophosphoric acid mono- or diester of lauryl alcohol tetraethyleneglycol ether, stearyl alcohol, phenol hexaethyleneglycol ether or a mixture of such orthophosphoric acid mono- and diesters.

4. Red phosphorus as claimed in claim 1, wherein the homogeneous blend contains the salt in a proportion of 0.25 to 3 weight %.

5. Red phosphorus as claimed in claim 1, wherein the aliphatic alcohol or phenol is ethoxylated.

6. In a process for making stabilized red phosphorus consisting of a homogeneous blend of red phosphorus particles with a size of at most about 2 mm and as an oxidation stabilizer the aluminum, magnesium, calcium or zinc salt of an acid orthophosphoric acid ester of a long chain aliphatic alcohol or phenol, the improvement which comprises: intimately blending red phosphorus particles with a size of at most about 2 mm with about 0.25 to 5 weight % of an acid orthophosphoric acid ester of a long chain aliphatic alcohol or phenol; suspending the blend in water and heating the resulting suspension to about 60° to 95° C; gradually admixing the suspension with at least stoichiometric proportions of an aqueous solution of a water-soluble aluminum, magnesium, calcium or zinc salt; filtering the resulting mixture, and drying the filter residue at elevated temperature.

7. The process as claimed in claim 6, wherein the red phosphorus particles have a size of about 0.01 to 0.15 mm.

8. The process as claimed in claim 6, wherein the aliphatic alcohol or phenol is ethoxylated.

9. The process as claimed in claim 6, wherein the aqueous suspension of red phosphorus has a temperature of 80° to 90° C.

10. The process as claimed in claim 6, wherein the acid orthophosphoric acid ester is the orthophosphoric acid mono- or diester of lauryl alcohol tetraethyleneglycol ether, stearyl alcohol, phenolhexaeythyleneglycol ether or a mixture of such orthophosphoric acid mono- and diesters.

11. The process as claimed in claim 6, wherein the red phosphorus is blended with 1 to 3 weight % of the acid orthophosphoric acid ester of lauryl alcohol tetraethyleneglycol ether.

12. The process as claimed in claim 6, wherein the water-soluble salt is $Al_2(SO_4)_3 \cdot 18\ H_2O$, $Ca(NO_3)_2 \cdot 4\ H_2O$, $ZnSO_4 \cdot 7\ H_2O$ or $MGSO_4 \cdot 7\ H_2O$.

13. The process as claimed in claim 6, wherein the water-soluble aluminum, magnesium, calcium or zinc salt is used in the form of a 5 to 20 weight % aqueous solution.

14. The process as claimed in claim 6, wherein the zinc salt of the orthophosphoric acid ester is precipitated from the aqueous suspension at a pH-value of 5.0 to 5.5.

15. The process as claimed in claim 6, wherein the calcium salt of the orthophosphoric acid ester is precipitated from the aqueous suspension at a pH-value of 7.0 to 7.5.

16. The process as claimed in claim 6, wherein the magnesium salt of the orthophosphoric acid ester is precipitated from the aqueous suspension at a pH-value of 7.0 to 7.5.

17. The process as claimed in claim 6, wherein the filter residue is dried at a temperature of 80° to 130° C.

* * * * *